United States Patent [19]

Hübsch et al.

[11] Patent Number: 5,137,881
[45] Date of Patent: Aug. 11, 1992

[54] SUBSTITUTED PYRIDO-OXAZINE INHIBITORS OF HMG-COA REDUCTASE

[75] Inventors: Walter Hübsch; Rolf Angerbauer; Peter Fey; Hilmar Bischoff, all of Wuppertal, Fed. Rep. of Germany; Joachim Bender, Lafayette, Calif.; Delf Schmidt, Wuppertal, Fed. Rep. of Germany

[73] Assignee: Bayer Aktiengesellschaft, Leverkusen, Fed. Rep. of Germany

[21] Appl. No.: 730,404

[22] Filed: Jul. 16, 1991

[30] Foreign Application Priority Data

Jul. 21, 1990 [DE] Fed. Rep. of Germany ....... 4023308

[51] Int. Cl.$^5$ .................. A61K 31/435; C07D 498/04
[52] U.S. Cl. ..................................... 514/81; 514/302; 546/23; 546/116
[58] Field of Search .................... 546/23, 116; 514/81, 514/302

[56] References Cited

U.S. PATENT DOCUMENTS

| | | | |
|---|---|---|---|
| 4,518,602 | 5/1985 | Terao et al. | 514/332 |
| 4,874,775 | 10/1989 | Krumkalns et al. | 514/357 |
| 4,977,161 | 12/1990 | Fujikawa et al. | 546/116 |

FOREIGN PATENT DOCUMENTS 0397044  5/1990  Fed. Rep. of Germany.

*Primary Examiner*—Bernard Dentz
*Attorney, Agent, or Firm*—Sprung Horn Kramer & Woods

[57] ABSTRACT

Substituted pyrido-oxazines can be prepared by reduction of the corresponding ketones. They are useful active compounds in medicaments, in particular for the treatment of hyperlipoproteinaemia, lipoproteinaemia and arteriosclerosis.

10 Claims, No Drawings

SUBSTITUTED PYRIDO-OXAZINE INHIBITORS OF HMG-COA REDUCTASE

The invention relates to substituted pyrido-oxazines, to intermediate compounds for their preparation, and to their preparation and their use in medicaments.

It is known that lactone derivatives isolated from fungal cultures are inhibitors of 3-hydroxy-3-methyl-glutarylcoenzyme A reductase (HMG-CoA reductase) [mevinolin, EP 22,478; U.S. Pat. No. 4,231,938].

Phosphorus-containing HMG-CoA reductase inhibitors having antihypercholesterolaemic activity are additionally published in DE 3,817,298 Al.

New substituted pyrido-oxazines of the general formula (I)

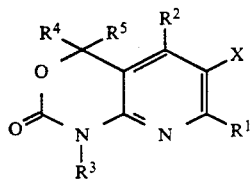

in which
$R^1$ represents straight-chain or branched alkyl having up to 8 carbon atoms, or represents cycloalkyl having 3 to 6 carbon atoms,
$R^2$ represents phenyl which is optionally monosubstituted or disubstituted by identical or different substituents from the series comprising straight-chain or branched alkyl having up to 6 carbon atoms, trifluoromethyl, hydroxymethyl, phenoxy, benzyl, benzyloxy or halogen,
$R^3$ represents hydrogen, represents straight-chain or branched alkyl having up to 10 carbon atoms, which is optionally substituted by cyano, alkoxy having up to 6 carbon atoms, phenyl, pyridyl, thienyl, furyl, quinolyl or naphthyl, represents straight-chain or branched alkenyl or alkynyl in each case having up to 8 carbon atoms, or represents cycloalkyl having 3 to 6 carbon atoms,
$R^4$ and $R^5$ are identical or different and represent hydrogen, or represent straight-chain or branched alkyl having up to 8 carbon atoms, which is optionally substituted by hydroxyl, halogen, cyano or alkoxy having up to 4 carbon atoms, and
X represents a radical of the formula —A—B, in which
A denotes a group of the formula —CH$_2$—CH$_2$— or —CH=CH—, and
B denotes a group of the formula

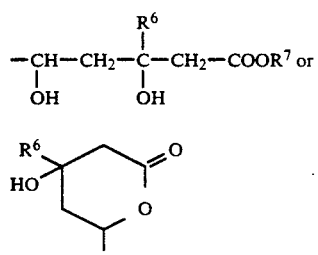

in which
$R^6$ denotes hydrogen or straight-chain or branched alkyl having up to 10 carbon atoms and
$R^7$ denotes hydrogen or straight-chain or branched alkyl having up to 10 carbon atoms, which can be substituted by phenyl, or denotes aryl having 6 to 10 carbon atoms or a cation,
or represents a radical of the formula

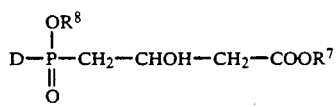

in which
D denotes a radical of the formula —(CH$_2$)$_t$, —CH=CH—, —C≡C— or —CH$_2$—O—, in which the latter is bonded to the phosphorus atom via O,
t denotes the number 1 or 2,
$R^7$ has the abovementioned meaning, and
$R^8$ denotes hydrogen or straight-chain or branched alkyl having up to 4 carbon atoms or a cation,
and their salts have been found.

If $R^7$ forms an ester radical with the carboxyl group, a physiologically tolerable ester radical is preferably meant by this, which is easily hydrolyzed in vivo to give a free carboxyl group and a corresponding physiologically tolerable alcohol. These include, for example, alkyl esters (C$_1$ and C$_6$) and aralkyl esters (C$_7$ to C$_{10}$), preferably (C$_1$–C$_4$)-alkyl esters and benzyl esters. Moreover, the following ester radicals may be mentioned: methyl esters, ethyl esters, propyl esters and benzyl esters.

If $R^7$ represents a cation, a physiologically tolerable metal cation or ammonium cation is preferably meant. Preferred cations in this connection are alkali metal cations or alkaline earth metal cations such as, for example, lithium sodium, potassium, magnesium or calcium cations, and also aluminum or ammonium cations, as well as non-toxic substituted ammonium cations formed from amines such as (C$_1$–C$_4$)-dialkylamines, (C$_1$–C$_4$)-trialkylamines, procaine, dibenzylamine, N,N'-dibenzylethylethylenediamine, N-benzyl-β-phenylethylamine, N-methylmorpholine or N-ethylmorpholine, 1-ephenamine, dihydroabietylamine, N,N'-bis-dihydroabietylethylenediamine, N-lower alkylpiperidine and other amines which can be used for the formation of salts.

$R^8$ can likewise represent one of the abovementioned physiologically tolerable metal cations or ammonium cations.

Surprisingly, the substituted pyrido-oxazines according to the invention show a superior inhibitory action on HMG-CoA reductase (3-hydroxy-3-methyl-glutaryl-coenzyme A reductase).

Preferred compounds of the general formula (I) are those in which
$R^1$ represents straight-chain or branched alkyl having up to 6 carbon atoms, or represents cyclopropyl, cyclopentyl or cyclohexyl,
$R^2$ represents phenyl which is optionally substituted by straight-chain or branched alkyl having up to 4 carbon atoms, trifluoromethyl, fluorine, chlorine or bromine,
$R^3$ represents hydrogen, represents straight-chain or branched alkyl having up to 8 carbon atoms, which is optionally substituted by cyano, alkoxy having up to 4 carbon atoms, phenyl or pyridyl, represents straight-chain or branched alkenyl having up to 6 carbon atoms, or represents cyclopropyl, cyclopentyl or cyclohexyl, $R^4$ and $R^5$ represent hydrogen, and X represents a radical of the formula —A—B, in which A denotes a group of the formula —CH$_2$—CH$_2$— or —CH=CH—, and B denotes a group of the formula

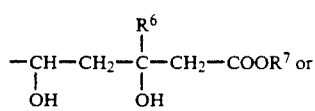

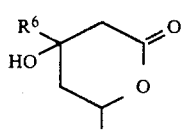

in which $R^6$ denotes hydrogen and $R^7$ denotes hydrogen or straight-chain or branched alkyl having up to 8 carbon atoms or benzyl, or denotes phenyl or a cation, and their salts.

Particularly preferred compounds of the general formula (I) are those in which $R^1$ represents straight-chain or branched alkyl having up to 4 carbon atoms or cyclopropyl, $R^2$ represents phenyl which is optionally substituted by methyl, trifluoromethyl, fluorine or chlorine, $R^3$ represents hydrogen, represents straight-chain or branched alkyl having up to 6 carbon atoms, which is optionally substituted by cyano, phenyl or pyridyl, or represents straight-chain or branched alkenyl having up to 4 carbon atoms, $R^4$ and $R^5$ represent hydrogen, and X represents a radical of the formula —A—B, in which A denotes the —CH=CH— or 13 CH$_2$—CH$_2$— group, and B denotes a group of the formula

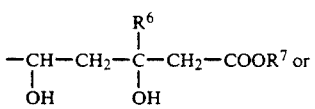

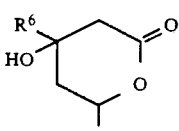

in which $R^6$ denotes hydrogen and $R^7$ denotes hydrogen, methyl, ethyl, propyl, isopropyl, butyl, isobutyl, tert-butyl or benzyl, or denotes a sodium, potassium, calcium, magnesium or ammonium ion, and their salts.

The substituted pyrido-oxazines of the general formula (I) according to the invention have several asymmetric carbon atoms and can therefore exist in various stereochemical forms. The invention relates both to the individual isomers and to their mixtures.

Depending on the meaning of the radicals given under the substituent X, different stereoisomers result, which will be explained as exemplified by the radical —A—B in the following:

a) If the group —A— represents a group of the formula —CH=CH—, the compounds according to the invention can exist in two stereoisomeric forms which can have the E-configuration (II) or Z-configuration (III) of the double bond:

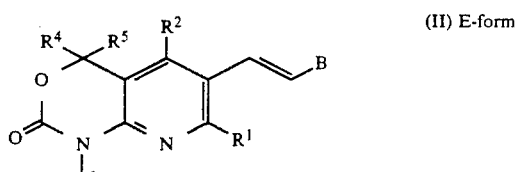
(II) E-form

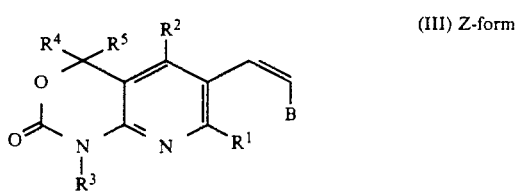
(III) Z-form in which $R^1$, $R^2$, $R^3$, $R^4$, $R^5$ and B have the abovementioned meanings.

Preferred compounds of the general formula (I) are those which have the E-configuration (II).

b) If the radical —B represents a group of the formula

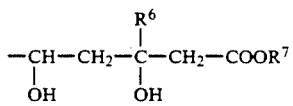

the compounds of the general formula (I) have at least two asymmetric carbon atoms, namely the two carbon atoms to which the hydroxyl groups are bonded. Depending on the relative position of these hydroxyl groups to one another, the compounds according to the invention can be present in the erythro-configuration (IV) or in the threo-configuration (V).

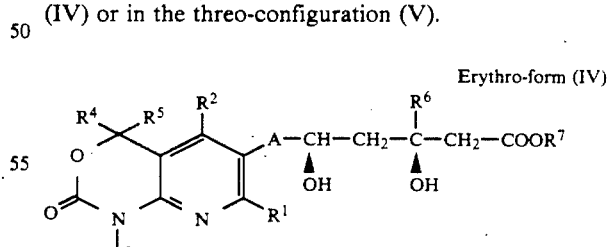
Erythro-form (IV)

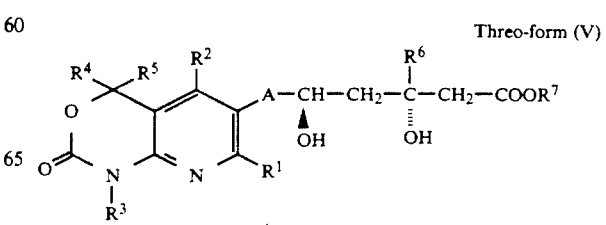
Threo-form (V)

In each case, two enantiomers, namely the 3R,5S-isomer or the 3S,5R-isomer (erythro-form) and the 3R,5R-isomer and the 3S,5S-isomer (threo-form) in turn exist both of the compounds in the erythro- and in the threo-configuration.

The isomers in the erythro-configuration are preferred in this case, particularly preferably the 3R,5S-isomer and the 3R,5S-3S,5R-racemate.

c) If the radical —B represents a group of the formula

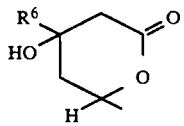

the substituted pyrido-oxazines have at least two asymmetric carbon atoms, namely the carbon atom to which the hydroxyl group is bonded, and the carbon atom to which the radical of the formula

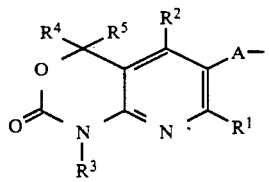

is bonded. Depending on the position of the hydroxyl group to the free valency on the lactone ring, the substituted pyrido-oxazines can be present as cis-lactones (VI) or as trans-lactones (VII).

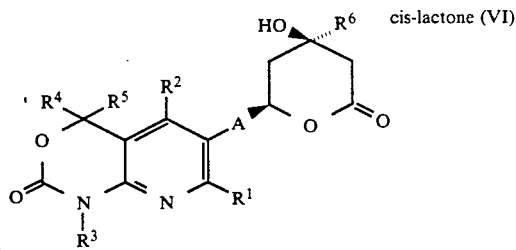
cis-lactone (VI)

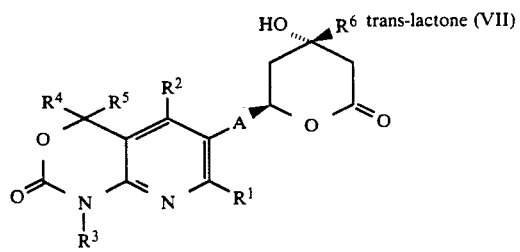
trans-lactone (VII)

In each case, two isomers, namely the 4R, 6R-isomer or the 4S,6S-isomer (cis-lactone), and the 4R,6S-isomer or the 4S,6R-isomer (trans-lactone) in turn exist both of the cis-lactone and the trans-lactone. Preferred isomers are the trans-lactones. The 4R,6S-isomer (trans) and the 4R,6S-4S,6R-racemate are particularly preferred in this case.

The following isomeric forms of the substituted pyridooxazines may be mentioned as examples:

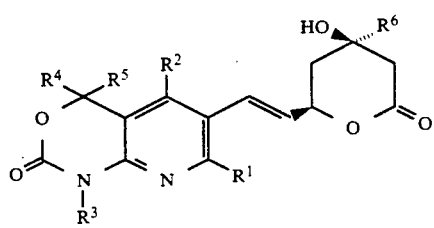

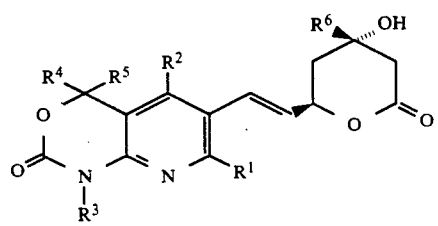

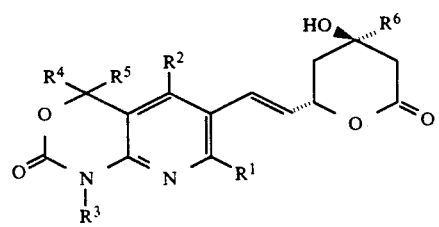

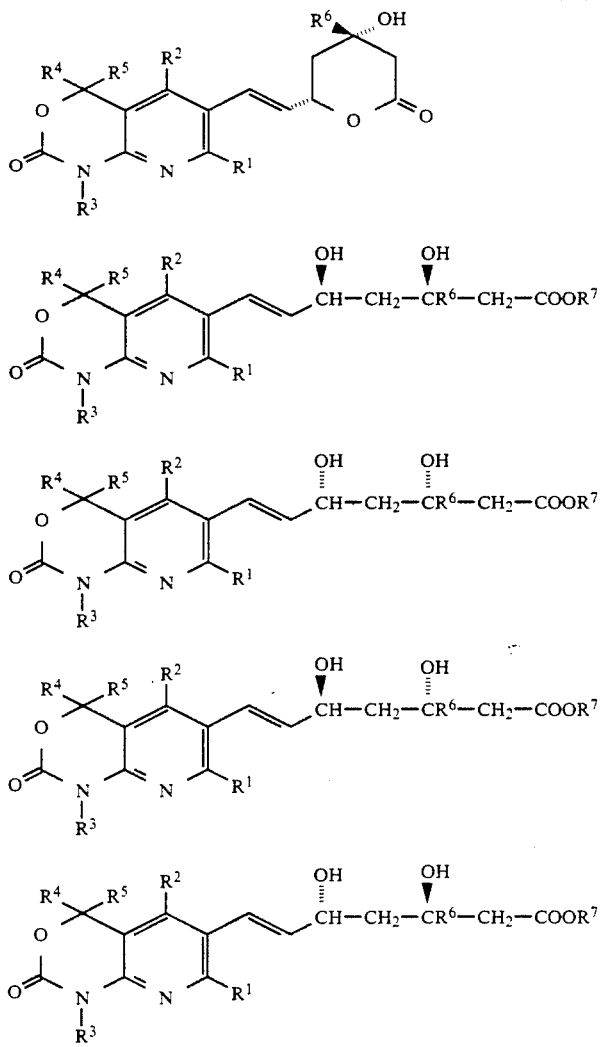

A process for the preparation of the substituted pyridooxazines of the general formula (I)

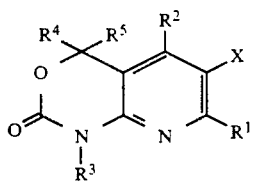

(I)

in which

R$^1$, R$^2$, R$^3$, R$^4$ and R$^5$ have the abovementioned meanings, has been found, characterized in that ketones of the general formula (VIIIa)

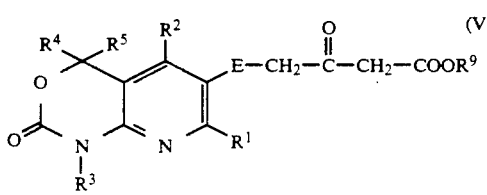

(VIII)

in which

R$^1$, R$^2$, R$^3$, R$^4$ and R$^5$ have the abovementioned meanings,

R$^9$ represents alkyl, and

E represents a group

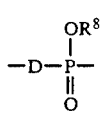

(VIIIa)

or

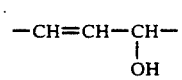

(VIIIb)

are reduced, in the case of the preparation of the acids, the esters are hydrolyzed, in the case of the preparation of the lactones, the carboxylic acids are cyclized, in the case of the preparation of the ethylene compounds (A=—CH$_2$—CH$_2$—), the ethene compounds (A=—CH=CH—) are hydrogenated by customary methods, and, if appropriate, isomers are separated.

The process according to the invention can be illustrated by the following reaction scheme:

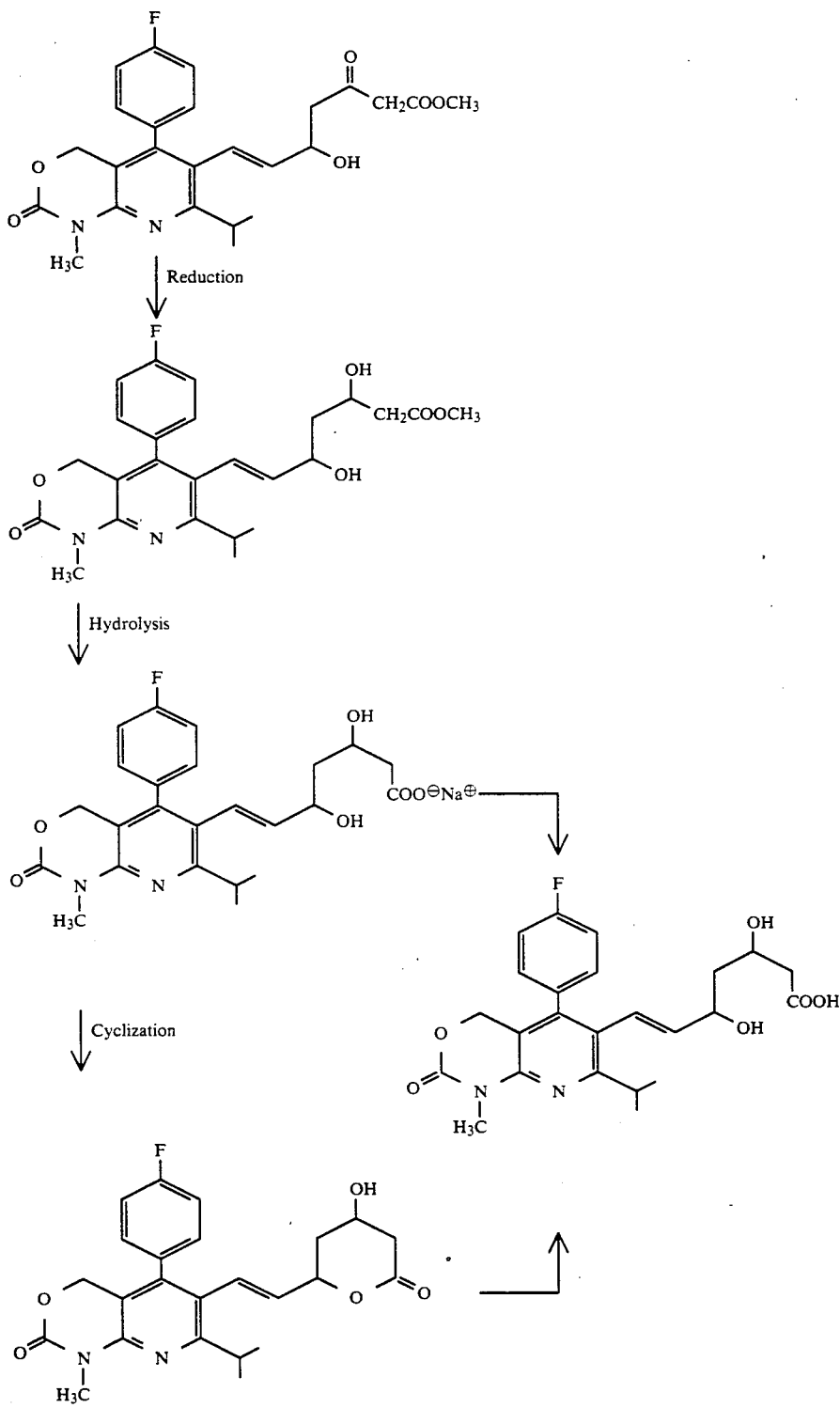

The reduction can be carried out with the customary reducing agents, preferably with those which are suitable for the reduction of ketones to hydroxyl compounds. In this case, reduction with metal hydrides or complex metal hydrides in inert solvents, if appropriate in the presence of a trialkylborane, is particularly suitable. The reduction is preferably carried out with complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminum hydride. The reduction is very particularly preferably carried out with sodium borohydride in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenohydrocarbons such as, for example, dichloromethane, trichloromethane, tetrachloromethane, 1,2-dichloroethane, or hydrocarbons such as, for example, benzene, toluene or xylene. It is also possible to employ mixtures of the solvents mentioned.

If E represents the radical of the formula (VIIIa), alcohols such as methanol, ethanol or propanol, preferably ethanol, are employed.

The reduction of the ketone group to the hydroxyl group is particularly preferably carried out under conditions in which the other functional groups such as, for example, the alkoxycarbonyl group, are not changed.

The use of sodium borohydride as the reducing agent is particularly suitable for this purpose, in the presence of triethylborane in inert solvents such as, preferably, ethers.

The reduction is in general carried out in a temperature range from −80° C. to +30° C., preferably from −78° C. to 0° C.

The process according to the invention is in general carried out at normal pressure. However, it is also possible to carry out the process at reduced pressure or at elevated pressure (for example in a range from 0.5 to 5 bar).

In general, the reducing agent is employed in an amount from 1 to 2 mols preferably from 1 to 1.5 mols relative to 1 mol of the keto compound.

Under the abovementioned reaction conditions, the carbonyl group is in general reduced to the hydroxyl group without reduction of the double bond to a single bond taking place.

In order to prepare compounds of the general formula (I) in which A represents an ethylene grouping, the reduction of the ketones (VIII) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ia)

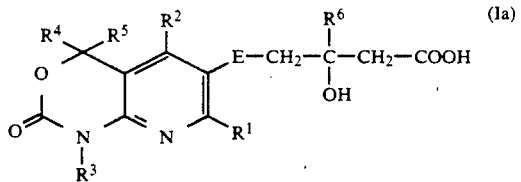

in which

R$^1$, R$^2$, R$^3$, R$^4$, R$^5$, R$^6$ and E have the abovementioned meanings.

The carboxylic acid esters in the context of the general formula (I) correspond to the formula (Ib)

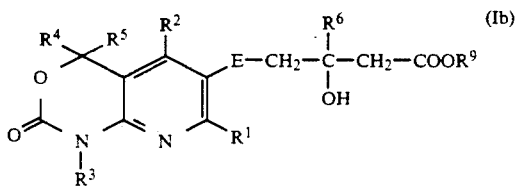

in which

R$^1$, R$^2$, R$^3$, R$^4$, R$^5$, R$^6$ and E have the abovementioned meanings. and R$^9$ represents alkyl.

The salts of the compounds according to the invention in the context of the general formula (I) correspond to the formula (Ic)

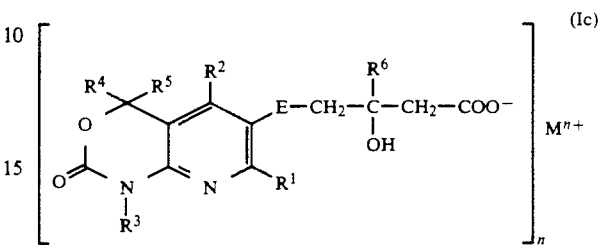

in which

R$^1$, R$^2$, R$^3$, R$^4$, R$^5$, R$^6$ and E have the abovementioned meanings, and M$^{n+}$ represents a cation.

The lactones in the context of the general formula (I) correspond to the formula (Id)

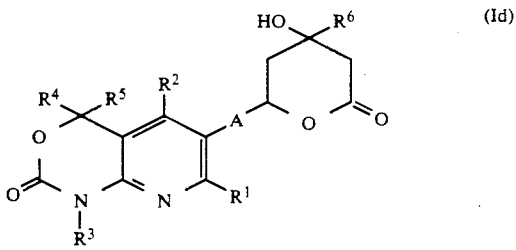

in which

R$^1$, R$^2$, R$^3$, R$^4$, R$^5$, R$^6$ and A have the abovementioned meanings.

In order to prepare the carboxylic acids of the general formula (Ia) according to the invention, the carboxylic acid esters of the general formula (Ib) or the lactones of the general formula (Id) are in general hydrolyzed by customary methods. The hydrolysis is in general carried out by treating the esters or the lactones with customary bases in inert solvents, the salts of the general formula (Ic) in general being formed first, which can then be converted into the free acids of the general formula (Ia) in a second step by treatment with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert-butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range of 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mols, preferably from 1 to 1.5 mols, relative to 1 mol of the ester or the lactone. Molar amounts of the reactants are particularly preferably used.

When carrying out the reaction, the salts (Ic) of the compounds according to the invention are formed in the first step as intermediates which can be isolated. The acids (Ia) according to the invention are obtained by treating the salts (Ic) with customary inorganic acids. These preferably include mineral acids such as, for example, hydrochloric acid, hydrobromic acid, sulphuric acid or phosphoric acid. In this connection, it has proved advantageous in the preparation of the carboxylic acids (Ia) to acidify the basic reaction mixture from the hydrolysis in a second step without isolating the salts. The acids can then be isolated in a customary manner.

In order to prepare the lactones of the formula (Id) according to the invention, the carboxylic acids (Ib) according to the invention are in general cyclized by customary methods, for example by heating the corresponding acids in inert organic solvents, if appropriate in the presence of molecular sieves.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of the solvents mentioned. Hydrocarbons are particularly preferably used, in particular toluene, in the presence of molecular sieves.

The cyclization is in general carried out in a temperature range from −40° C. to +200° C., preferably from −25° C. to +50° C.

The cyclization is in general carried out at normal pressure, but it is also possible to carry out the process at reduced pressure or at elevated pressure (for example in a range from 0.5 to 5 bar).

Moreover, the cyclization is also carried out in inert organic solvents, with the aid of cyclizing or dehydrating agents. Carbodiimides are preferably used in this case as dehydrating agents. The preferred carbodiimides employed are N,N'-dicyclohexylcarbodiimide, N-cyclohexyl-N'-[2-(N"-methylmorpholinium)ethyl]-carbodiimide paratoluenesulphonate or N-(3-dimethylaminopropyl)-N'-ethylcarbodiimide hydrochloride.

Suitable solvents in this connection are the customary organic solvents. These preferably include ethers such as diethyl ether, tetrahydrofuran or dioxane, or chlorohydrocarbons such as methylene chloride, chloroform or carbon tetrachloride, or hydrocarbons such as benzene, toluene, xylene or mineral oil fractions. Chlorohydrocarbons such as, for example, methylene chloride, chloroform or carbon tetrachloride, or hydrocarbons such as benzene, tolune, xylene or mineral oil fractions are particularly preferred. Chlorohydrocarbons such as, for example, methylene chloride, chloroform or carbon tetrachloride are particularly preferably employed.

The reaction is in general carried out in a temperature range of from 0° C. to +80° C., preferably from +10° C. to +50° C.

When carrying out the cyclization, it has proved advantageous to employ the cyclization method using carbodiimides as dehydrating agents.

The separation of the isomers into the stereoisomerically homogeneous constituents is in general carried out by customary methods such as are described, for example, by E. L. Eliel, Stereochemistry of Carbon Compounds, McGraw Hill, 1962. In this connection, the separation of the isomers from the racemic lactone stage is preferred. The racemic mixture of the trans-lactones (VII) is particularly preferably converted in this case by treating either with D-(+)- or L-(−)-α-methylbenzylamine by customary methods into the diastereomeric dihydroxyamides (Ie)

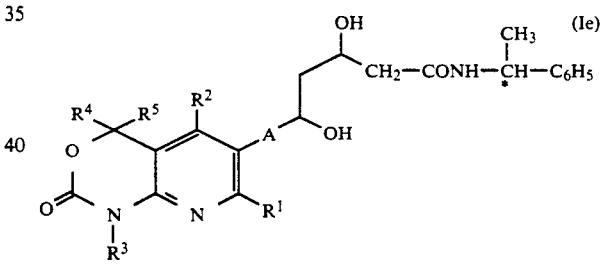

which can then be separated into the individual diastereomers by chromatography or crystallization, as is customary. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, gives the corresponding enantiomerically pure dihydroxy acids (Ia), which can be converted into the enantiomerically pure lactones by cyclization as described above. In general, it is true of the preparation of the compounds of the general formula (I) according to the invention in enantiomerically pure form that the configuration of the final products according to the method described above is dependent on the configuration of the starting materials.

The isomer separation is illustrated by way of example in the following scheme:

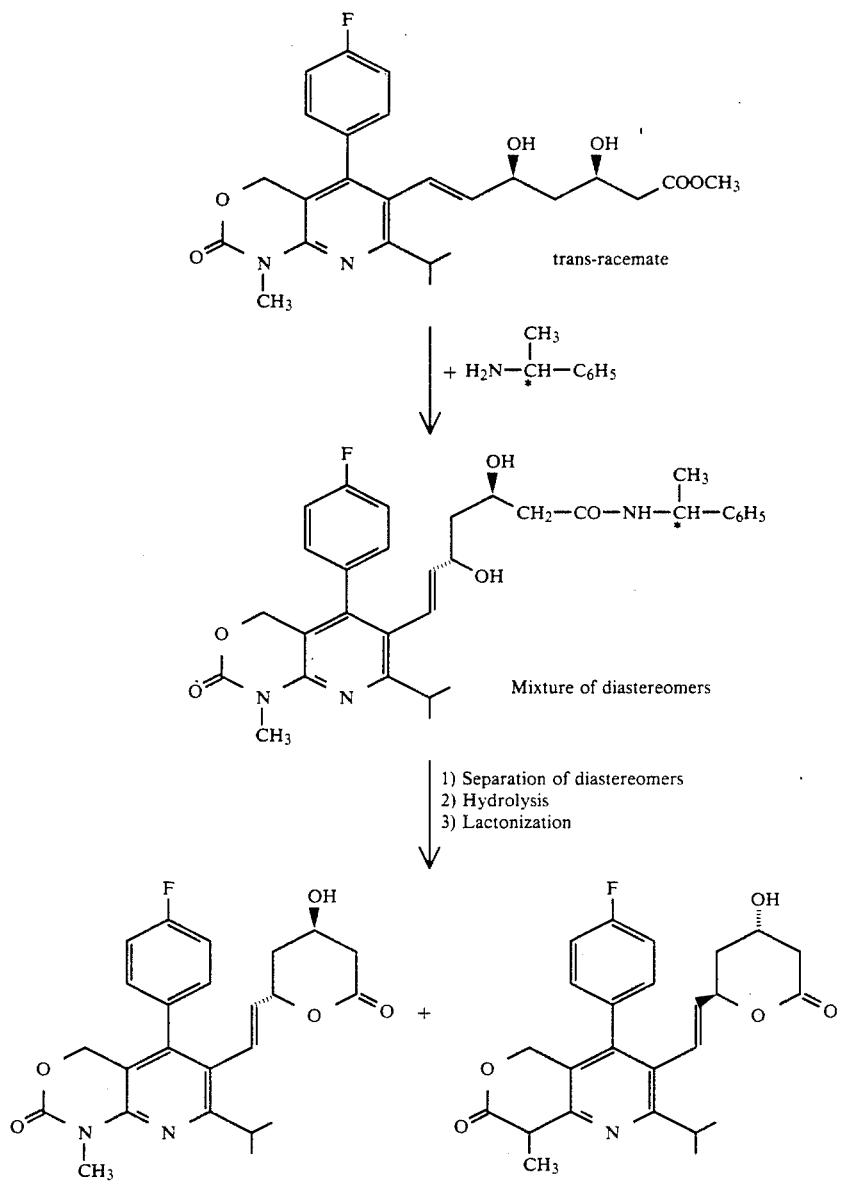

The ketones (VIII) employed as starting materials are new.

The ketones of the formula (VIIIa) are prepared in analogy to the process described in DE 3,817,298 Al.

The ketones of the general formula (VIIIb) according to the invention

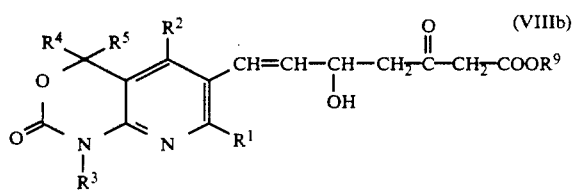 (VIIIb)

in which

R$^1$, R$^2$, R$^3$, R$^4$, R$^5$ and R$^9$ have the abovementioned meanings, are prepared by a process in which aldehydes of the general formula (IX)

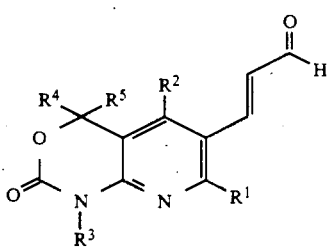 (IX)

in which

R$^1$, R$^2$, R$^3$, R$^4$ and R$^5$ have the abovementioned meanings, are reacted in inert solvents with acetoacetic acid esters of the general formula (X)

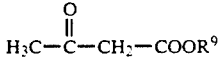 (X)

in which

R⁹ has the abovementioned meaning, in the presence of bases.

The process according to the invention can be illustrated, for example, by the following equation:

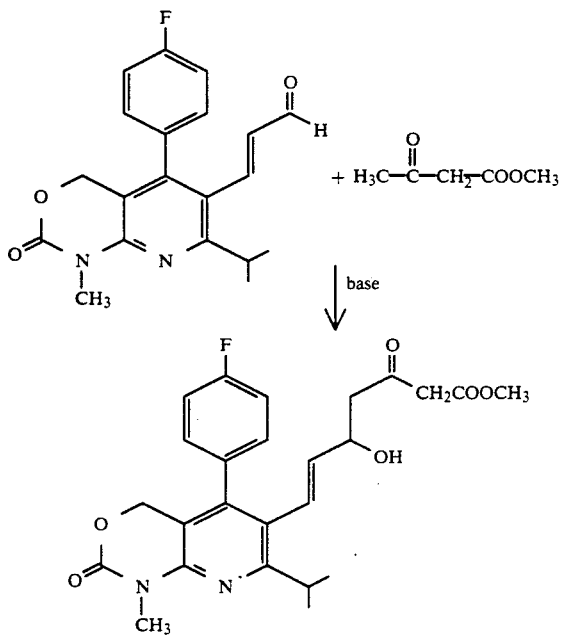

Suitable bases in this connection are the customary strongly basic compounds. These preferably include organolithium compounds such as, for example, n-butyllithium, sec-butyllithium, tert-butyllithium or phenyllithium, or amides, such as, for example, lithium diisopropylamide, sodium amide or potassium amide, or lithium hexamethyldisilylamide, or alkali metal hydrides such as sodium hydride or potassium hydride. It is also possible to employ mixtures of the bases mentioned. N-Butyllithium or sodium hydride or a mixture thereof is particularly preferably employed.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are particularly preferably used.

The reaction is in general carried out in a temperature range from −80° C. to +50° C., preferably from −20° C. to room temperature.

The process is in general carried out at normal pressure, but it is also possible to carry out the process at reduced pressure or at elevated pressure, for example in a range from 0.5 to 5 bar.

When carrying out the process, the acetoacetic acid ester is in general employed in an amount from 1 to 2, preferably from 1 to 1.5,mols, relative to 1 mol of the aldehyde.

The acetoacetic acid esters of the formula (X) employed as starting materials are known or can be prepared by known methods [Beilstein's Handbuch der organischen Chemie (Beilstein's Handbook of Organic Chemistry) III, 632;438].

Examples of acetoacetic acid esters which may be mentioned for the process according to the invention are: methyl acetoacetate, ethyl acetoacetate, propyl acetoacetate or isopropyl acetoacetate.

The preparation of the aldehydes of the general formula (IX) employed as starting materials is illustrated by way of example as follows for the case in which X represents the group —A—B:

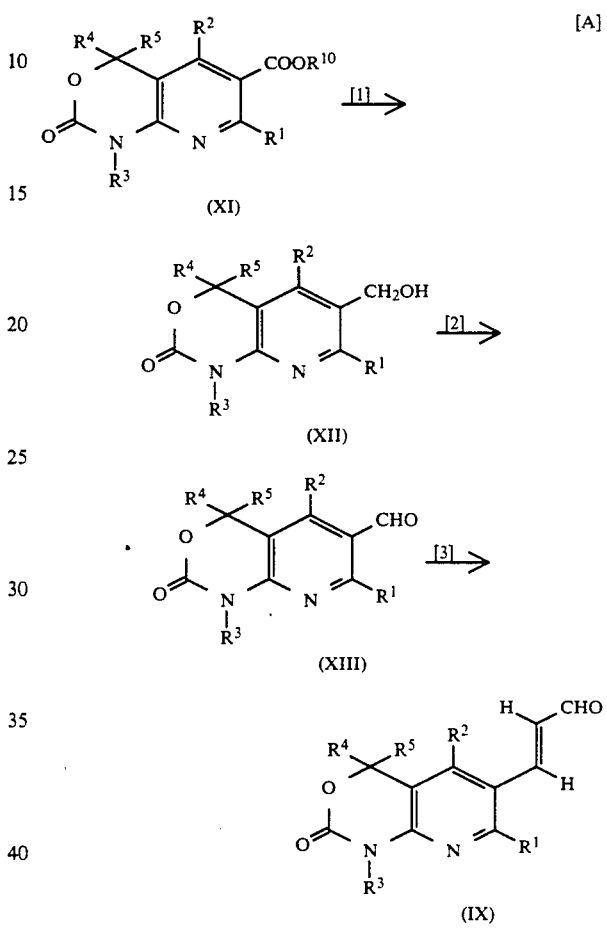

In this connection, according to scheme A, 2H-pyrido[2,3-d]-[1,3]-oxazines of the formula (XI), in which R¹⁰ represents alkyl having up to 4 carbon atoms, are reduced to the hydroxymethyl compounds (XII) in a first step [1] in inert solvents such as toluene or ethers, for example diethyl ether, tetrahydrofuran or dioxane, preferably tetrahydrofuran or toluene, using metal hydrides as reducing agents, for example lithium aluminum hydride, sodium cyanoborohydride, sodium aluminum hydride, diisobutylaluminum hydride or sodium bis-(2-methoxyethoxy)-dihydroaluminate, in temperature ranges from −70° C. to +100° C., preferably from −70° C. to room temperature, or from room temperature to 70° C., depending on the reducing agent used. Reduction is preferably carried out with diisobutylaluminum hydride in toluene in a temperature range from −78° C. to room temperature. The hydroxymethyl compounds (XII) are oxidized to the aldehydes (XIII) by customary methods in a second step [2]. The oxidation can be carried out, for example, with pyridinium chlorochromate, optionally in the presence of alumina, in inert solvents such as chlorohydrocarbons, preferably methylene chloride, in a temperature range from 0° C. to 60° C., preferably at room temperature, or else with trifluoroacetic anhydride/dimethyl sulphoxide by the customary methods of Swern oxidation. The aldehydes (XIII) are reacted to give the aldehydes (IX) in a third step [3] with diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range from −20° C. to 40° C., preferably from room temperature to 70° C.

The 2H-pyrido[2,3-d]-[1,3]oxazines (XI) employed as starting materials in this connection are in the case in which $R^4$ and $R^5$ denote hydrogen (XIa), obtained according to scheme [B], by first oxidizing the dihydropyridines of the formula (XIV), in which $R^{10}$ and $R^{10'}$ are identical or different and have the abovementioned meaning, to the corresponding pyridines of the formula (XV), then converting the ester function (COOR') into the corresponding hydroxymethyl compounds (XVI) by reduction and in a last step cyclizing by conventional methods and in the case in which $R^4$ and/or $R^5$ are different from hydrogen, for example, first reacting the compounds of the general formula (XV) with Grignard compounds according to a customary method and then cyclizing.

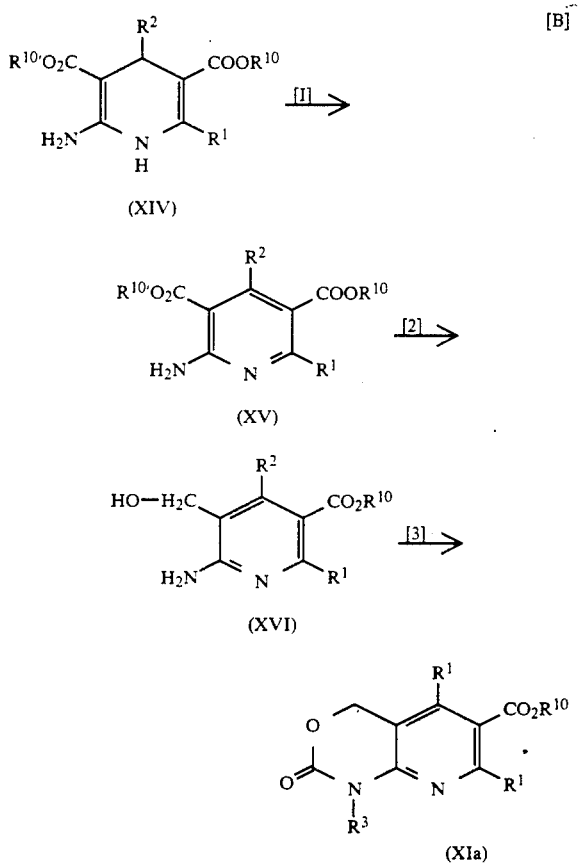

[B]

The oxidation of the dihydropyridines (XIV) to give the pyridines (XV) can be carried out, for example, with chromic oxide in glacial acetic acid in a temperature range from −20° C. to +150° C., preferably at reflux temperature, or with 2,3-dichloro-5,6-dicyano-p-benzoquinone as the oxidizing agent in inert solvents such as chlorohydrocarbons, preferably methylene chloride, in a temperature range from 0° C. to +100° C., preferably at room temperature.

The reduction to give the hydroxymethyl compounds of the formula (XVI) [step 2] is carried out using suitable reducing agents, such as, for example, lithium aluminum hydride, diisobutyl aluminum hydride or sodium bis-(2-methoxyethoxy)-dihydroaluminate in inert solvents, such as, for example, tetrahydrofuran.

The cyclization is carried out using carbonic acid derivatives such as, for example, phosgene, di- or triphosgene, chloroformic acid esters or carbonic acid esters such as, for example, diphenyl carbonate with addition of bases such as, for example, alkali metal hydroxides, alkali metal alkoxides, tertiary amines or using 1,8-diazabicyclo-[5.4.0]-undec-7-ene, 1,4-diazabicyclo[2.2.2]octane or 1,5-diazabicyclo[4.3.0]non-5-ene. 1,8-Diazabicyclo[5.4.0]-undec-7-ene is preferred.

The base is employed in an amount from 1 to 3 mol equivalents, preferably from 1 to 2 mol equivalents.

The dihydropyridines of the general formula (XIV) are in some cases new or are known and can be prepared by known methods, for example by condensation of ethoxycarbonylacetamidine hydrochloride and (E)-Z-1-(4-fluorophenyl)-2-methoxycarbonyl-4-methyl-pent-1-en-3-one.

The compounds of the general formula (I) according to the invention have useful pharmacological properties and can be employed in medicaments. In particular, they are inhibitors of 3-hydroxy-3-methyl-glutaryl-coenzyme A (HMG-CoA) reductase and, as a result of this, inhibitors of cholesterol biosynthesis. They can therefore be employed for the treatment of hyperlipoproteinaemia, lipoproteinaemia or atherosclerosis. The active compounds according to the invention additionally cause a lowering of the cholesterol content in the blood.

The enzyme activity determination was carried out as modified by G. C. Ness et al., Archives of Biochemistry and Biophysics 197, 493–499 (1979). Male Rico rats (body weight 300–400 g) were treated with altromin powdered feed, to which 40 g of colestyramine/kg of feed had been added, for 11 days. After decapitation, the livers were removed from the animals and placed on ice. The livers were comminuted and homogenized 3 times in a Potter-Elvejem homogenizer in 3 volumes of 0.1M sucrose, 0.05M KCl, 0.04 M $K_xH_y$ phosphate, 0.03M ethylene-diaminetetraacetic acid, 0.002M dithiothreitol (SPE) buffer pH 7.2. The mixture was then centrifuged at 15,000 g for 15 minutes and the sediment was discarded. The supernatant was sedimented at 100,000 g for 75 minutes. The pellet was taken up in ¼ volumes of SPE buffer, homogenised again and then centrifuged again at 100,000 g for 60 minutes. The pellet was taken up using a 5-fold amount of its volume of SPE buffer, homogenized and frozen and stored at −78° C. (=enzyme solution).

For testing, the test compounds (or mevinolin as a reference substance) were dissolved in dimethylformamide with the addition of 5 vol.% of 1N NaOH and employed in the enzyme test using 10 μl in various concentrations. The test was begun after 20 minutes pre-incubation of the compounds with the enzyme at 37° C. The test mixture amounted to 0.380 ml and contained 4 μmol of glucose 6-phosphate, 1.1 mg of bovine serum albumin, 2.1 μmol of dithiothreitol, 0.35 μmol of NADP, 1 unit of glucose 6-phosphate dehydrogenase, 35 μmol of $K_xH_y$ phosphate pH 7.2, 20 μl of enzyme preparation and 56 nmol of 3-hydroxy-3-methyl-glutaryl coenzyme A (glutary-3-$^{14}$C) of 100,000 dpm.

After an incubation of 60 minutes at 37° C., the mixture was centrifuged and 600 μl of the supernatant was applied to a 0.7×4 cm column packed with a 5-chloride 100-200 mesh (anion exchanger). The column was washed with 2 ml of distilled water and 3 ml of Aquasol was added to the runnings plus washing water and counted in an LKB scintillation counter. $IC_{50}$ values were determined by intrapolation by plotting the percentage inhibition against the concentration of the compound in the test. In order to determine the relative inhibitory potency, the $IC_{50}$ value of the reference substance mevinolin was set at 1 and compared with the simultaneously determined $IC_{50}$ value of the test compound.

| Example No. | in vitro relative activity $IC_{50}$, Mevinolin = 1 |
|---|---|
| 1 a | 3 |
| 1 b | 20 |
| 1 c | 13 |
| 1 d | 66 |
| 1 e | 66 |
| 2 b | 24 |
| 2 e | 50 |

The present invention also includes pharmaceutical preparations which, in addition to inert, non-toxic, pharmaceutical auxiliaries and excipients, contain one or more compounds of the general formula (I), or which consist of one or more active compounds of the formula (I), and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations can also contain other pharmaceutical active compounds.

The abovementioned pharmaceutical preparations can be prepared by known methods in a customary manner, for example using the auxiliary or auxiliaries or excipient(s).

In general, it has proved advantageous to administer the active compound(s) of the formula (I) in total amounts of about 0.0005 to about 20 mg/kg, preferably in total amounts of about 0.001 mg/kg to 5 mg/kg of body weight every 24 hours, if desired in the form of several individual doses, to achieve the desired results.

However, it may be advantageous to deviate from the amounts mentioned, in particular depending on the species and body weight of the subject to be treated, on individual behavior towards the medicament, the nature and severity of the disease, the type of preparation and administration, and the time or interval at which administration takes place.

Starting compounds

EXAMPLE I (E)-Z-I-(4-Fluorophenyl)-2-methoxycarbonyl-4-methyl-pent-1-en-3-one

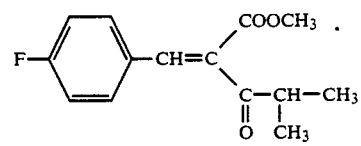

A solution of 22.5 ml (0.227 mol) of piperidine and 13.5 ml (0.236 mol) of acetic acid in 100 ml of isopropanol is added to 576.7 g (4 mol) of methyl isobutyrylacetate and 496.5 g (4 mol) of 4-fluorobenzaldehyde in 1 l of isopropanol. The mixture is stirred at room temperature for 1 day and concentrated in vacuo, and the residue is distilled in a high vacuum.

Yield: 840.7 g (84% of theory) of yellowish oil.
B.p.: 150°–152° C. (4 mbar).

EXAMPLE II

2-Amino-3-ethoxycarbonyl-4-(4-fluorophenyl)-6-isopropyl-5-methoxycarbonyl-1,4-dihydropyridine

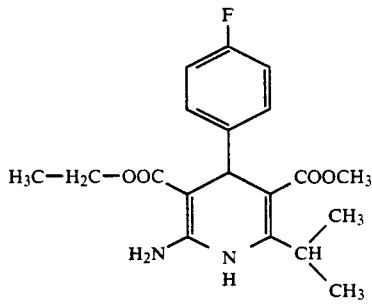

66.6 g (0.4 mol) of ethyl 3,3-diaminoacrylate hydrochloride and 100 g (0.4 mol) of the compound from Example I are heated to reflux overnight with 44 ml (0.4 mol) of N-methylmorpholine in 800 ml of isopropanol. The mixture is concentrated in vacuo and the residue is chromatographed in a column (φ20 cm) on 2 kg of silica gel 230–400 mesh using petroleum ether/ethyl acetate (2:1).

Yield: 109.7 g (75.7% of theory) of colorless crystals M.p.: 161° C. (from ether/petroleum ether)

EXAMPLE III

Amino-3-ethoxycarbonyl-4-(4-fluorophenyl)-6-isopropyl-5-methoxycarbonyl-pyridine

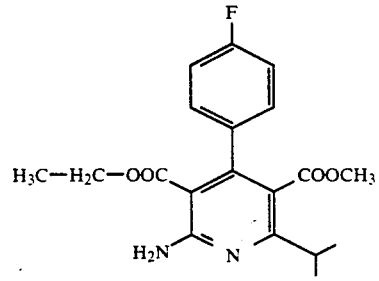

22.7 g (0.1 mol) of 2,3-dichloro-4,5-dicyano-benzoquinone are added to a solution of 36.2 g (0.1 mol) of the compound from Example II in 2 l of dichloromethane and the mixture is stirred at room temperature for 40 min. The suspension is filtered through 1.5 kg of silica gel 230-400 mesh in a glass suction filter and washed using a mixture of petroleum ether/ethyl acetate 2:1. The eluate is concentrated in vacuo and the residue which remains is thoroughly stirred in ether/petroleum ether and filtered off with suction.

Yield: 31.6 g (88% of theory).
M.p 141° C.

EXAMPLE IV

2-Amino-4-(4-fluorophenyl)-3-hydroxymethyl-6-isopropyl-5-methoxycarbonyl-pyridine

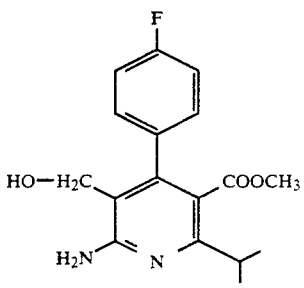

100 ml (0.35 mol) of a 3.5M solution of sodium bis-(2-methoxy-ethoxy)-dihydroaluminate in toluene are initially introduced under argon into 100 ml of tetrahydrofuran p.a. 63 g (175 mmol) of the compound from Example III dissolved in 700 ml of tetrahydrofuran are added dropwise and the mixture is subsequently stirred at 30° C. for 1 h. 2 l of water are cautiously added dropwise. The phases are separated and the aqueous phase is washed twice with 700 ml of ethyl acetate. The combined organic phases are washed with 500 ml of saturated sodium chloride solution and dried using sodium sulphate. The solution is filtered and concentrated in vacuo. The residue is chromatographed in a column ($\phi$ 6 cm) on 400 g of silica gel 230-400 mesh using petroleum ether/ethyl acetate (1:1). The eluate is concentrated in vacuo and the residue is thoroughly stirred in ether/petroleum ether.

Yield: 45.2 g (81.2% of theory) of colorless crystals.
M.p.: 137° C.

EXAMPLE V 5-(4-Fluorophenyl)-7-isopropyl-6-methoxycarbonyl-2-oxo-1,4-dihydro-2H-pyrido-[2,3-d][1,3]oxazine

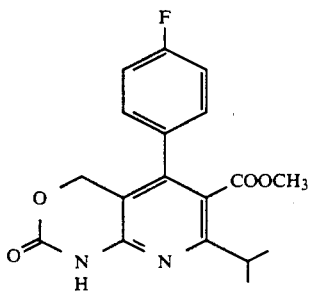

41.3 g (0.13 mol) of the compound from Example IV are dissolved in 325 ml of toluene and heated to reflux with 33.4 g (156 mmol) of diphenyl carbonate and 21.7 g (143 mmol) of 1,8-diazabicyclo-[5.4.0]-undec-7-ene for 30 min. The mixture is cooled and treated with 300 ml of water and 150 ml of ethyl acetate. The aqueous phase is extracted with 300 ml of ethyl acetate and the combined organic phases are washed twice with 200 ml of 0.1M NaOH and once with 200 ml of saturated sodium chloride solution, dried using sodium sulphate and concentrated in vacuo. The residue which remains is chromatographed in a column ($\phi$ 20 cm) on 1.6 kg of silica gel 230-400 mesh using a mixture of petroleum ether/ethyl acetate (3:1) to (1:1).

Yield: 16.6 g (37.1% of theory) of colorless crystals.
M.p.: 175° C.

EXAMPLE VI 5-(4-Fluorophenyl-7-isopropyl-6-hydroxymethyl-2-oxo-1,4-dihydro-2H-pyrido[2,3-d][1,3]oxazine

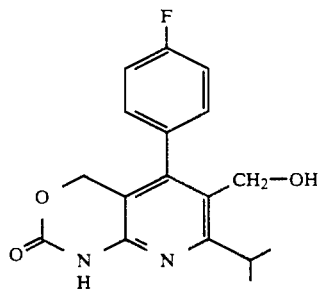

100 ml of a 1.5M solution of diisobutylaluminum hydride in toluene are slowly added at −75° C. under argon to a solution of 17.2 g (50 mmol) of the compound from Example V in 700 ml of toluene. After 1 h, 33 ml of 1.5M diisobutylaluminum hydride solution are added at the same temperature, the mixture is stirred for a further hour and 33 ml of 1.5M diisobutylaluminum hydride solution are added again. The mixture is stirred at −75° C. for 2 h and then allowed to warm to room temperature, being treated cautiously with 250 ml of water and 250 ml of ethyl acetate from −30° C. The mixture is filtered off with suction through kieselguhr, which is washed with ethyl acetate. After phase separation, the aqueous phase is extracted with ethyl acetate, and the combined organic phases are washed with saturated sodium chloride solution, dried over sodium sulphate and concentrated in vacuo. The residue which remains is stirred thoroughly in dichloromethane and filtered off with suction. 2.2 g (13.9% of theory) of the title compound are obtained. The mother liquor is chromatographed in a column ($\phi$ 6 cm) on 400 g of silica gel 230-400 mesh using a gradient of petroleum ether/ethyl acetate (2:1 to 1:1). 1.1 g (6.9% of theory) of the title compound are obtained. The kieselguhr residue is boiled twice with 300 ml of acetate, filtered off with suction and the filtrate is concentrated in vacuo. 8.7 g (55% of theory) of the title compound are obtained.

Yield: 12.0 g (75.9% of theory) of colorless crystals.
M.p.: 154° C.

EXAMPLE VII 5-(4-Fluorophenyl)-6-formyl-7-isopropyl-2-oxo-1,4-dihydro-2H-pyrido[2,3-d][1,3]oxazine

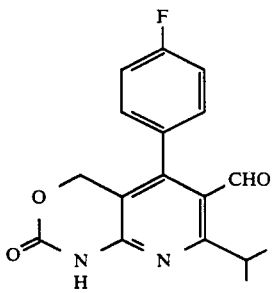

12 g (38 mmol) of the compound from Example VI are suspended in 1.4 l of dichloromethane, and the mixture is treated with 7.8 g of neutral alumina and 16.3 g (76 mmol) of pyridinium chlorochromate and stirred at room temperature for 1 h. The suspension is added to a glass frit (porosity 3) which contains 600 g of silica gel 230–400 mesh, and eluted without sucking dry using petroleum ether/ethyl acetate 2:1. The eluate is concentrated to dryness in vacuo and the residue which remains is stirred thoroughly in ether/petroleum ether.

Yield: 10.8 g (90.5% of theory).
M.p.: 157° C.

EXAMPLE VIII 5-(4-Fluorophenyl)-6-formyl-7-isopropyl-1-(1-picolyl)-2-oxo-1,4-dihydro-2H-pyrido[2,3-d][1,3]oxazine

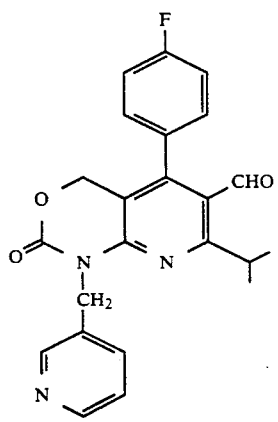

2.36 g (7.5 mmol) of the compound from Example VII are dissolved in 60 ml of anhydrous dimethylformamide and the mixture is treated with 1.77 g (15.8 mmol) of potassium tert-butoxide. It is stirred at room temperature for 15 min and 1.36 g (8.25 mmol) of 3-picolyl chloride hydrochloride are added. The mixture is stirred at 60° C. for 100 min and then poured into 200 ml of ice-water. The mixture is extracted twice with ethyl acetate, and the combined organic phases are washed with saturated sodium chloride solution, dried over sodium sulphate and concentrated in vacuo. The residue which remains is chromatographed in a column (φ4 cm) on 100 g of silica gel 230–400 mesh using a mixture of petroleum ether/ethyl acetate of 2:1 to 1:1.

Yield: 1.0 g (32% of theory) of colorless crystals.
M.p.: 124° C. (from ether).

EXAMPLE IX 5-(4-Fluorophenyl)-6-formyl-7-isopropyl-1-methyl-2-oxo-1,4-dihydro-2H-pyrido[2,3-d][]1,3]oxazine

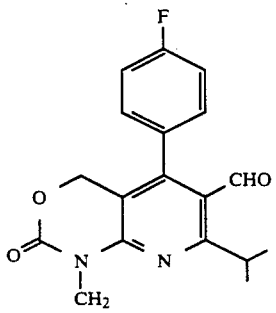

0.3 g (10 mmol) of 80% strength sodium hydride is suspended in 12 ml of anhydrous tetrahydrofuran under a gentle stream of argon, and the mixture is treated with 2.5 g (8 mmol) of the compound from Example VII in 20 ml of tetrahydrofuran. The mixture is stirred at room temperature for 15 min and 1.5 ml (24 mmol) of methyl iodide are added dropwise. The mixture is stirred at 40 to 50° C. for 90 min, cooled, treated cautiously with water and extracted twice with ethyl acetate. The combined organic phases are washed with saturated sodium chloride solution, dried over sodium sulphate and concentrated to dryness in vacuo. The residue which remains is stirred thoroughly in ether/petroleum ether and filtered off with suction.

Yield: 1.98 g (75% of theory) of colorless crystals.
M.p. 147° C.

EXAMPLE X

1-Benzyl-5-(4-fluorophenyl)-6-formyl-7-isopropyl-2-oxo-1,4-dihydro-2H-pyrido[2,3-d][1,3]oxazine

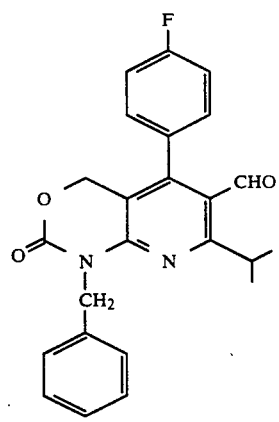

2.36 g (7.5 mmol) of the compound from Example VII are dissolved in 20 ml of anhydrous dimethylformamide, and the mixture is treated with 0.28 g (9.4 mmol) of 80% strength sodium hydride under a gentle stream of argon. The mixture is stirred at room temperature for 15 min and treated with 1.54 g (9 mmol) of benzyl bromide. After 60 min, 30 ml of water are cautiously added and the mixture is extracted twice with ethyl acetate. The combined organic phases are washed with saturated sodium chloride solution, dried over sodium sulphate and concentrated to dryness in vacuo. The residue which remains is chromatographed in a column (φ

3 cm) on 50 g of silica gel 230-400 mesh using petroleum ether/ethyl acetate 4:1.

Yield 2.3 g (75% of theory) of colorless amorphous solid.

$R_f=0.2$ (petroleum ether/ethyl acetate 5:1).

EXAMPLE XI

1-Allyl-5-(4-fluorophenyl)-6-formyl-7-isopropyl-2-oxo-1,4-dihydro-2H-pyrido[2,3][1,3]oxazine

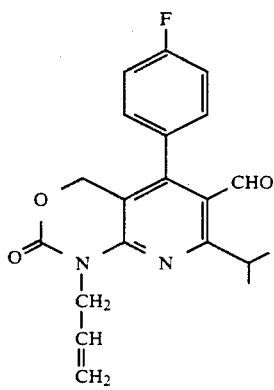

In analogy to Example X, 1.55 g (58% of theory) of the title compound are obtained using 1.1 g (9 mmol) of 3-bromopropene.

M.p.: 92° C. (from ether/petroleum ether).

EXAMPLE XII-a (E)-3-[5-(4-Fluorophenyl)-7-isopropyl-2-oxo-1,4-dihydro-2H-pyrido[2,3-d][1,3]oxazine-6-yl]prop-2-enal

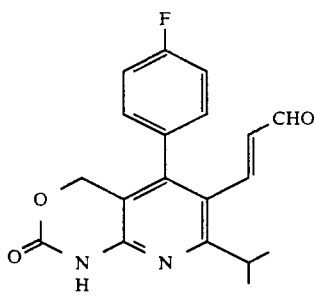

A solution of 2.5 g (9.6 mmol) of diethyl 2-(cyclohexyl-amino)-vinyl-phosphonate in 24 ml of tetrahydrofuran is added dropwise under argon at 0-5° C. in the course of 10 min to a suspension of 0.58 g (19.2 mmol) of 80% strength sodium hydride in 24 ml of anhydrous tetrahydrofuran. The mixture is stirred at 0° C. for 15 min, a solution of 2.5 g (8 mmol) of the compound from Example VII in 24 ml of tetrahydrofuran is added dropwise at 0°-5° C. in the course of 20 min, and the mixture is stirred at room temperature for 30 min and under reflux for 2 h. It is cooled, treated cautiously with 75 ml of water, extracted twice with ethyl acetate, and the combined organic phases are washed with saturated sodium chloride solution and concentrated in vacuo. The residue is heated to reflux with a mixture of 100 ml of toluene, 100 ml of water and 5.3 g (41.6 mmol) of oxalic acid dihydrate for 1 h. The mixture is cooled, 100 ml of ethyl acetate are added and the phases are separated. The aqueous phase is extracted twice with ethyl acetate, and the combined organic phases are washed with saturated sodium chloride solution, dried over sodium sulphate and concentrated in vacuum. The residue is chromatographed in a column ($\phi$ 4 cm) containing 100 g of silica gel 230-400 mesh using a mixture of petroleum ether/ethyl acetate 2:1 to ethyl acetate.

Yield: 0.85 g (31% of theory).

M.p.: 223° C.

The examples shown in Table 1 were prepared in analogy to the procedure for Example XII-a using 1.2 mol equivalents of sodium hydride:

TABLE 1

| Ex. No. | R | Starting material Example | Yield | M.p. (°C.) |
|---|---|---|---|---|
| XII-b | —CH₃ | IX | 60% | 122° C. |
| XII-c | —CH₂-pyridyl | VIII | 38% | yellowish amorphous |
| XII-d | —CH₂-phenyl | X | 54% | 179° C. |
| XII-e | —CH₂—CH=CH₂ | XI | 42% | 97° C. |

Preparation Examples (general Formula I)

EXAMPLE 1-a

Methyl erythro-(E)-7-[5-(4-fluorophenyl)-7-isopropyl-2-oxo-1,4-dihydro-2H-pyrido[2,3-d][1,3]oxazin6-yl]-3,5-dihydroxy-hept-6-enoate

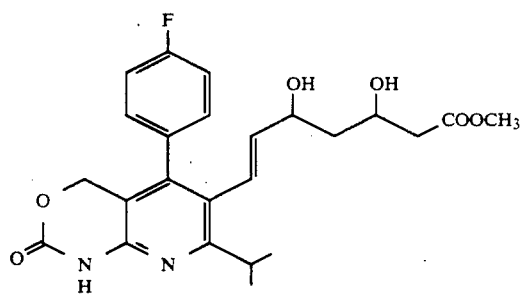

0.44 g (3.75 mmol) of methyl acetoacetate is added dropwise at 0°-5° C. to a suspension of 0.23 g (7.5 mmol) of 80% strength sodium hydride in 10 ml of anhydrous tetrahydrofuran. After 15 min, 4.7 ml (7.785 mmol) of 15% strength butyllithium in hexane are added dropwise in the course of 10 min and the mixture is kept at 0°-5° C. for a further 15 min. 0.85 g (2.5 mmol) of the compound from Example XII-a in 10 ml of tetrahydrofuran are then added and the mixture is stirred at room temperature for 30 min. The mixture is then treated cautiously with 0.96 g (16 mmol) of acetic acid in 25 ml of water and extracted three times with ethyl acetate, and the combined organic phases are washed with saturated sodium chloride solution, dried over sodium sulphate and concentrated in vacuo. The residue which remains is dissolved in 15 ml of anhydrous tetrahydrofuran. 3 ml of a 1M triethylborane solution in tetrahydrofuran are added and air is blown through the solution for 5 min. 114 mg (3 mmol) of sodium borohydride are added at −78° C. 2.5 ml of methanol is then added dropwise and the mixture is kept at −78° C. to −75° C. for 1 h. It is allowed to warm to room temperature, 8.3 ml of 30% strength hydrogen peroxide and 30 ml of water being added from −30° C. The mixture is extracted twice with ethyl acetate, and the combined organic phases are washed with saturated sodium chloride solution, dried over sodium sulphate and concentrated in vacuo. The residue which remains is chromatographed in a column (φ 3 cm) on 30 g of silica gel 230–400 mesh using petroleum ether/ethyl acetate (1:1).

Yield: 0.25 g (21% of theory) of amorphous solid.

$R_f$=0.28 (etny±acetate/petroleum ether 2:1).

$^1$H-NMR (CDCl$_3$) δ=7.65 (b, 1H); 7.2–7.0 (m, 4H); 6.35 (d, 1H); 5.3 (dd, 1H); 5.0 (s, 2H); 4.35 (m, 1H); 4.1 (m, 1H); 3.75 (s, 3H); 3.65 (b, 1H); 3.4–3.2 (m, 2H); 2.55–2.45 (m, 2H); 1.5–1.3 (m, 2H); 1.25 (d, 6H).

The compounds shown in Table 2 were prepared in analogy to Example 1-a, 2 mol equivalents of sodium hydride, 2.1 of butyllithium and 4.4 of acetic acid being used.

TABLE 2

| Ex. No. | R³ | Prepared from Example | Yield | M.p. (°C.) |
|---|---|---|---|---|
| 1-b | —CH₃ | XII-b | 30% | colorless amorphous |
| 1-c | —CH₂—(pyridyl) | XII-c | 3% | colorless oil |
| 1-d | —CH₂—(phenyl) | XII-d | 15% | colorless amorphous |
| 1-e | —CH₂—CH=CH₂ | XII-e | 12% | colorless oil |

EXAMPLE 2-b

Sodium erythro-(E)-7-[5-(4-fluorophenyl)-7-isopropyl-1-methyl-2-oxo-1,4-dihydro-2H-pyrido[2,3-d][1,3]oxazin-6-yl]-3,5-dihydroxy-hept-6-enoate

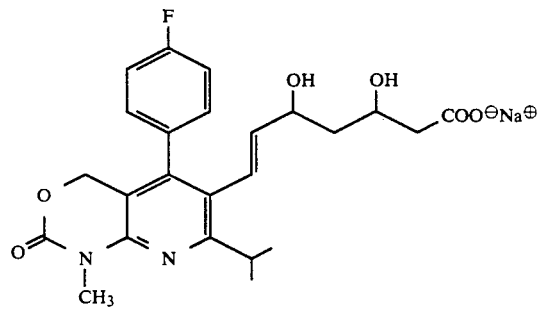

3 ml (0.3 mmol) of 0.1M sodium hydroxide solution are added to a solution of 142 mg (0.3 mmol) of the compound from Example 1-b in 3 ml of tetrahydrofuran and the mixture is stirred at room temperature for 1 h, concentrated to dryness in vacuo and the residue is dried over phosphorus pentoxide in a high vacuum.

Yield: 134 mg (93% of theory).

M.p.: 93° C. (dec.).

The compounds shown in Table 3 were prepared in analogy to the procedure of Example 2-b:

TABLE 3

| Ex. No. | R³ | Prepared from Example | Yield | M.p. (°C.) |
|---|---|---|---|---|
| 2-d | —CH₂—(phenyl) | 1-d | 71% | 123–125 (dec.) |
| 2-e | —CH₂—CH=CH₂ | 1-e | 94% | 127–130 (dec.) |

EXAMPLE 3-b

Methyl-7-(5-(4-fluorophenyl)-7-isopropyl-1-methyl-2-oxo-1,4-dihydro-2H-pyrido(2,3-d)(1,3)oxazine-6-yl)-3,5-dihydroxy-heptanoate

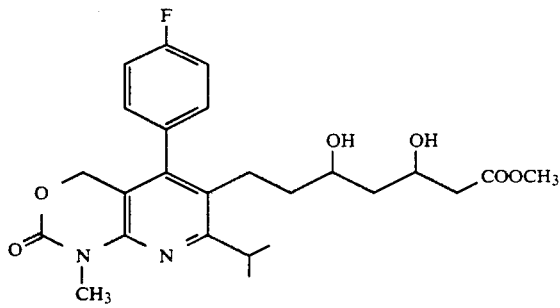

A solution of 153 mg (0.32 mmol) of the compound from Example 1-b in 25 ml of methanol and 20 μl of triethylamine are hydrogenated at room temperature and normal pressure for 4 hours over 120 mg of 10% palladium/carbon. The catalyst is filtered off, the solution is concentrated, the residue is dissolved in ethyl acetate and the solution is washed with saturated sodium chloride solution. The organic phase is dried and concentrated to dryness.

Yield: 123 mg (80% of theory) of colorless oil.

$^1$H-NMR (CDCl$_3$) δ=1.15-1.5 (m, 10H), 2.3-2.55 (m, 4H); 3.2 (m, 1H); 3.3 (b, 1H); 3.45 (s, 3H); 3.6 (m, 2H); 3.65 (s, 3H); 4.1 (m, 1H); 4.7 (m, 2H); 7.0-7.15 (m, 4H).

It will be understood that the specification and examples are illustrative but not limitative of the present invention and that other embodiments within the spirit and scope of the invention will suggest themselves to those skilled in the art.

We claim:

1. A substituted pyrido-oxazine of the formula

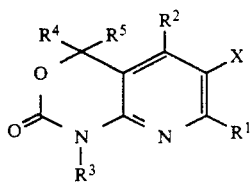 (I)

in which

R$^1$ represents straight-chain or branched alkyl having up to 8 carbon atoms, or represents cycloalkyl having 3 to 6 carbon atoms, R$^2$ represents phenyl which is optionally monosubstituted or disubstituted by identical or different substituents from the group consisting of straight-chain or branched alkyl having up to 6 carbon atoms, trifluoromethyl, hydroxymethyl, phenoxy, benzyl, benzyloxy and halogen, R$^3$ represents hydrogen, represents straight-chain or branched alkyl having up to 10 carbon atoms, which is optionally substituted by cyano, alkoxy having up to 6 carbon atoms, phenyl, pyridyl, thienyl, furyl, quinolyl or naphthyl, represents straight-chain or branched alkenyl or alkynyl in each case having up to 8 carbon atoms, or represents cycloalkyl having 3 to 6 carbon atoms, R$^4$ and R$^5$ are identical or different and represent hydrogen, or represent straight-chain or branched alkyl having up to 8 carbon atoms, which is optionally substituted by hydroxyl, halogen, cyano or alkoxy having up to 4 carbon atoms, X represents a radical of the formula —A—B, in which A denotes a group of the formula —CH$_2$—CH$_2$— or —CH=CH—, B denotes a group of the formula

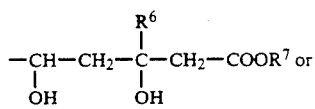

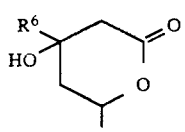

in which

R$^6$ denotes hydrogen or straight-chain or branched alkyl having up to 10 carbon atoms and R$^7$ denotes hydrogen or straight-chain or branched alkyl having up to 10 carbon atoms, which can be substituted by phenyl, or denotes aryl having 6 to 10 carbon atoms or a cation, or represents a radical of the formula

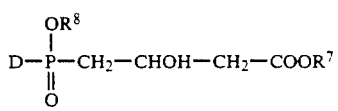

in which

D denotes a radical of the formula —(CH$_2$)$_t$, —CH=CH—, —C≡C— or —CH$_2$—O—, in which the latter is bonded to the phosphorus atom via O, t denotes the number 1 or 2, and R$^8$ denotes hydrogen or straight-chain or branched alkyl having up to 4 carbon atoms or a cation, or a salt thereof.

2. A substituted pyrido-oxazine or salt thereof according to claim 1, in which

R$^1$ represents straight-chain or branched alkyl having up to 6 carbon atoms, represents cyclopropyl, cyclopentyl or cyclohexyl, R$^2$ represents phenyl which is optionally substituted by straight-chain or branched alkyl having up to 4 carbon atoms, trifluoromethyl, fluorine, chlorine or bromine, R$^3$ represents hydrogen, represents straight-chain or branched alkyl having up to 8 carbon atoms, which is optionally substituted by cyano, alkoxy having up to 4 carbon atoms, phenyl or pyridyl, represents straight-chain or branched alkenyl having up to 6 carbon atoms, or represents cyclopropyl, cyclopentyl or cyclohexyl, R$^4$ and R$^5$ represent hydrogen, X represents a radical of the formula —A—B, in which A denotes a group of the formula —CH$_2$—CH$_2$— or —CH=CH—, B denotes a group of the formula

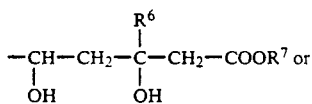

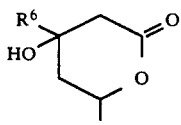

in which

R⁶ denotes hydrogen and

R⁷ denotes hydrogen or straight-chain or branched alkyl having up to 8 carbon atoms or benzyl, or denotes phenyl or a cation.

3. A substituted pyrido-oxazine or salt thereof according to claim 1, in which

R¹ represents straight-chain or branched alkyl having up to 4 carbon atoms or cyclopropyl, R² represents phenyl which is optionally substituted by methyl, trifluoromethyl, fluorine or chlorine, R³ represents hydrogen, represents straight-chain or branched alkyl having up to 6 carbon atoms, which is optionally substituted by cyano, phenyl or pyridyl, or represents straight-chain or branched alkenyl having up to 4 carbon atoms, R⁴ and R⁵ represent hydrogen, X represents a radical of the formula —A—B, in which A denotes the —CH=CH— or —CH₂—CH₂— group, B denotes a group of the formula

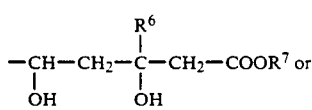

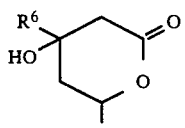

in which

R⁶ denotes hydrogen and

R⁷ denotes hydrogen, methyl, ethyl, propyl, isopropyl, butyl, isobutyl, tert-butyl or benzyl, or denotes a sodium, potassium, calcium, magnesium or ammonium ion.

4. A compound according to claim 1, wherein such compound is methyl-erythro-(E)-7-[1-benzyl-5-(4-fluorophenyl)-7-isopropyl-2-oxo-1,4-dihydro-2H-pyrido[2,3-d][1,3]oxazin-6-yl]-3,5-dihydroxy-hept-6-enoate of the formula

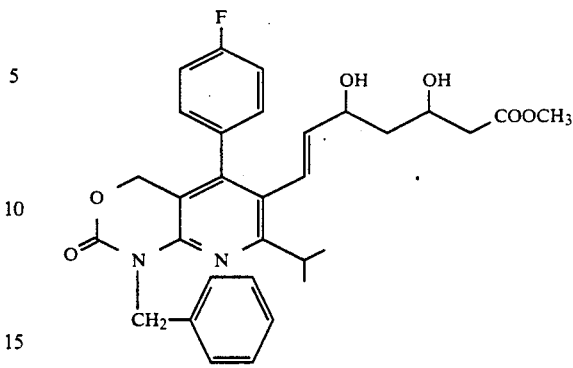

5. A compound according to claim 1, wherein such compound is methyl-erythro-(E)-7-[1-allyl-5-(4-fluorophenyl)-7-isopropyl-2-oxo-1,4-dihydro-2H-pyrido[2,3-d][1,3]oxazine-6-yl]-3,5-dihydroxy-hept-6-enoate of the formula

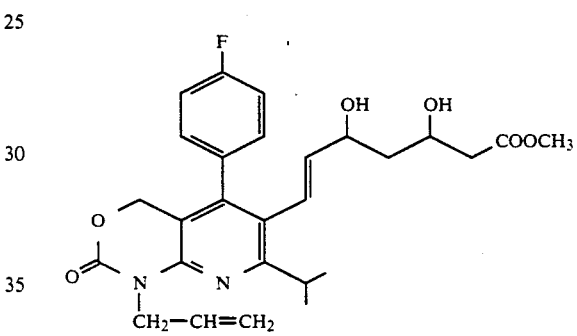

6. A compound according to claim 1, wherein such compound is sodium-erythro-(E)-7-[5-[4-fluorophenyl)-7-isopropyl-1-benzyl-2-oxo-1,4-dihydro-2H-pyrido[2,3-d][1,3]oxazin-6-yl]-3,5-dihydroxy-hept-6-enoate of the formula

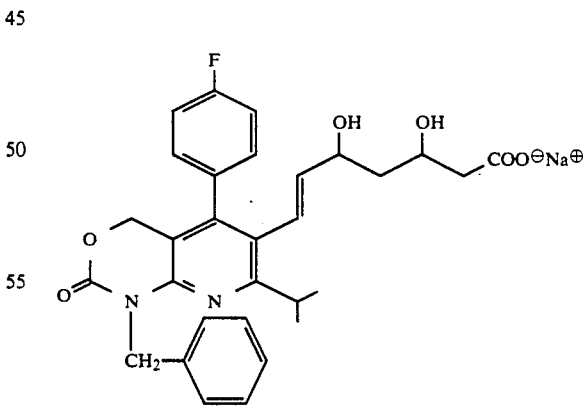

or a salt thereof.

7. A compound according to claim 1, wherein such compound is sodium-erythro-(E)-7-[5(4-fluorophenyl)-7-isopropyl-1-allyl-2-oxo-1,4-dihydro-2H-pyrido[2,3-d][1,3]oxazin-6-yl]-3,5-dihydroxy-hept-6-enoate of the formula

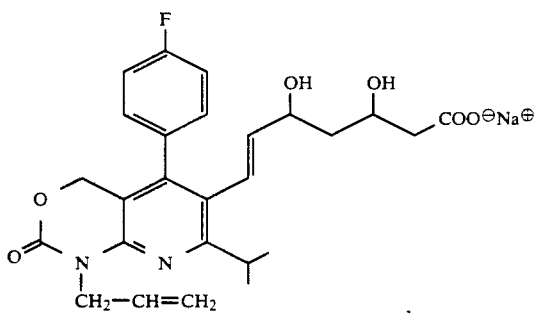

or a salt thereof.

8. A composition for the treatment of hyperlipoproteinaemia, lipoproteinaemia and arteriosclerosis comprising an amount effective therefor of a compound or salt thereof according to claim 1 and a pharmaceutically acceptable diluent.

9. A method of treating hyperlipoproteinaemia, lipoproteinaemia or arteriosclerosis in a patient afflicted therewith which comprises administering to such patient an amount effective therefor of a compound or salt thereof according to claim 1.

10. The method according to claim 9, wherein such compound is
methyl-erythro-(E)-7-[1-benzyl-5(4-fluorophenyl)-7-isopropyl-2-oxo-1,4-dihydro-2H-pyrido[2,3-d][1,3]oxazin-6-yl]-3,5-dihydroxy-hept-6-enoate,
methyl-erythro-(E)-7-[1-allyl-5-(4-fluorophenyl)-7-isopropyl-2-oxo-1,4-dihydro-2H-pyrido[2,3-d][1,3]oxazin-6-yl]-3,5-dihydroxy-hept-6-enoate,
7-sodium-erythro-(E)-[5-(4-fluorophenyl)-7-isopropyl-1-benzyl-2-oxo-1,4-dihydro-2H-pyrido[2,3-d][1,3]oxazin-6-yl]-3,5-dihydroxy-hept-6-enoate or a salt thereof, or
7-sodium-erythro-(E)-5-(4-fluorophenyl)-7-isopropyl-1-ally-2-oxo-1,4-dihydro-2H-pyrido[2,3-d][1,3]oxazin-6-yl]-3,5-dihydroxy-hept-6- enoate a salt thereof.

* * * * *